United States Patent [19]

Böhner et al.

[11] 4,123,437
[45] Oct. 31, 1978

[54] PROCESS FOR PREPARING 1,2,4-TRIAZOLE DERIVATIVES

[75] Inventors: Beat Böhner, Binningen; Dag Dawes, Pratteln; Willy Meyer, Basel, all of Switzerland

[73] Assignee: Ciba-Geigy Corporation, Ardsley, N.Y.

[21] Appl. No.: 773,026

[22] Filed: Feb. 28, 1977

Related U.S. Application Data

[60] Continuation of Ser. No. 587,500, Jun. 16, 1975, abandoned, which is a division of Ser. No. 420,121, Nov. 29, 1973, abandoned.

[30] Foreign Application Priority Data

Dec. 8, 1972 [CH] Switzerland .................. 17897/72

[51] Int. Cl.² .................. C07D 249/12; C07F 9/65
[52] U.S. Cl. .................. 260/308 R; 260/308 C; 424/200
[58] Field of Search .................. 260/308 R, 308 C

[56] References Cited

U.S. PATENT DOCUMENTS

| 3,701,784 | 10/1972 | Seidel et al. | 260/308 R |
| 3,862,125 | 1/1975 | Hoffman et al. | 260/308 R |

OTHER PUBLICATIONS

Elderfield, Heterocyclic Compounds, vol. 7, p. 440 (New York, 1961).
Arndt et al., Ber. Deut. Chem. Gesellschaft, vol. 76, pp. 2276–2283 (1923).

*Primary Examiner*—Alton D. Rollins
*Attorney, Agent, or Firm*—Harry Falber

[57] ABSTRACT

1,2,4-triazole derivatives which have particular importance as intermediates for, e.g., the preparation of active substances for pest control, corresponding to the formula

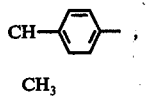

wherein
R¹ represents an unsubstituted or substituted alkyl, alkenyl, or alkynyl, naphthyl, benzyl, phenylethyl,

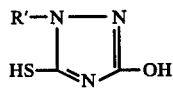

or phenylpropyl radical, or a mono or polycyclic cycloalkyl radical which can be bound by way of an alkylene bridge member, or a substituted phenyl radical, and new processes for the preparation of compounds of the formula

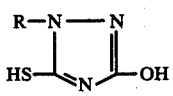

wherein R represents hydrogen, an optionally substituted alkyl, alkenyl or alkynyl radical, an optionally substituted phenyl, naphthyl, benzyl, phenylethyl or phenylpropyl radical, a mono- or polycyclic cycloalkyl radical which can be bound by way of an alkylene bridge member and/or be substituted by alkyl, or a partially hydrogenated naphthyl radical, which processes are performed by addition to a hydrazine of the formula

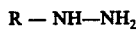

or to a hydrazone of the formula

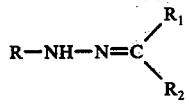

wherein R has the above given meaning, R₁ represents hydrogen or lower alkyl and R₂ represents lower alkyl, of an alkoxy-carbonyl-isothiocyanate of the formula

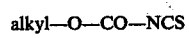

and subsequent closure of the triazole ring in the resulting thiosemicarbazide of the formula

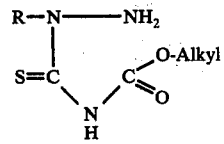

by the splitting-off of an alkanol (alkyl—OH), are disclosed.

5 Claims, No Drawings

PROCESS FOR PREPARING 1,2,4-TRIAZOLE DERIVATIVES

This is a continuation of application Ser. No. 587,500 filed On June 16, 1975, now abandoned which in turn, is a divisional of application Ser. No. 420,121, filed on Nov. 29, 1973, now abandoned.

The present invention relates to 1,2,4-triazole derivatives which have particular importance as intermediates for, e.g., the preparation of active substances for pest control.

The new 1,2,4-triazoles correspond to the formula

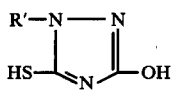 (Id)

wherein

R' represents an unsubstituted or substituted alkyl, alkenyl or alkynyl, naphthyl, benzyl, phenylethyl,

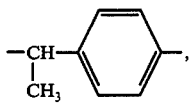

or phenylpropyl radical, or a mono- or polycyclic cycloalkyl radical which can be bound by way of an alkylene bridge member, or a substituted phenyl radical.

The present invention relates also to new processes for the preparation of compounds of the formula

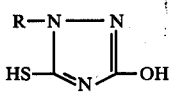 (I)

wherein R represents hydrogen, an optionally substituted alkyl, alkenyl or alkynyl radical, an optionally substituted phenyl, naphthyl, benzyl, phenylethyl or phenylpropyl radical, a mono- or polycyclic cycloalkyl radical which can be bound by way of an alkylene bridge member and/or be substituted by alkyl, or a partially hydrogenated naphthyl radical.

Alkyl radicals denoted by R' and R are straight-chain or branched-chain radicals having 1 to 18 carbon atoms, such as, e.g. the methyl, ethyl, n-propyl, isopropyl, n-butyl, sec.-butyl, isobutyl or tert.-butyl radical, pentyl, hexyl, octyl, decyl, dodecyl, tetradecyl, cetyl or octadecyl radicals, and isomers thereof; particularly lower alkyl radical having 1 to 6 carbon atoms can be substituted; for example, by: halogen (fluorine, chlorine, bromine or iodine), cyano, nitro, thiocyano, alkoxycarbonyl, N,N-dialkyl- and N-alkyl-carbamoyl, alkoxy, alkylthio, acylamino, alkylsulphonyl and alkylsulphinyl. Alkenyl or alkynyl radicals denoted by R' and R can be straight-chain or branched-chain radicals having 3 to 8 carbon atoms in a straight chain; those preferred are propenyl, butenyl, propinyl or butinyl, which can be substituted by methyl or ethyl. Suitable substituents of the aforementioned aromatic radicals in the case of R' and R (phenyl and naphthyl) as well as of the araliphatic radicals are: halogen (fluorine, chlorine or bromine), haloalkyl, nitro or alkyl; a phenyl radical can, in addition, be substituted by cyano, thiocyano, alkoxy, alkylthio, alkylsulphinyl, alkylsulphonyl or acylamino, or by phenyl or benzyl radicals bound by way of oxygen, sulphur or the SO— or $SO_2$-group, and optionally substituted by halogen, haloalkyl and/or alkyl. The aromatic and araliphatic radicals denoted by R' and R can be mono- or polysubstituted by the stated radicals. Where R' and R stand for cycloalkyl radicals, these are, in particular, monocyclic radicals having 3 to 8 ring carbon atoms, which can be substituted by lower alkyl, such as methyl ethyl or isopropyl, and/or be bound by way of the methylene bridge member or a polymethylene bridge member. Examples of such radicals are cyclopropyl, cyclobutyl, cyclopentyl or cyclohexyl.

The 1,2,4-triazoles of formula I obtainable by the process according to the invention can be in the following tautomeric forms:

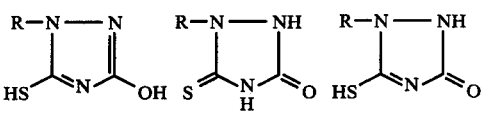

(Ia)      (Ib)      (Ic)

For reasons of consistency and simplicity, the compounds are represented in this description as corresponding to the formula Ia, both with regard to their representation by formula and with regard to the chemical denotation thereof.

The process according to the invention is performed by addition to a hydrazine of the formula

 (II)

of an alkoxycarbonyl-isothiocyanate of the formula alkyl—O—CO—NCS      (III);

and subsequent closure of the triazole ring in the resulting thiosemicarbazide of the formula

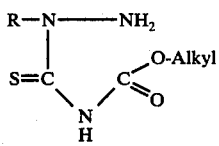 (IV)

by the splitting-off of an alkanol (alkyl OH).

These reactions can be performed in the presence or absence of solvents or diluents. For the obtainment of economic yields, it has proved advantageous to perform the addition — hydrazine component and isothiocyanate — in the presence of a solvent or diluent, whereby ketones, particularly acetone, have proved most suitable. There are, however, other substances, that are inert to the reactants, which are suitable as solvents and/or diluents, e.g. aliphatic and aromatic hydrocarbons or halogenated hydrocarbons, such as hexane, petroleum ether, chloroform, methylene chloride, halogenated ethanes, benzene, toluene, xylenes, ethers and ethereal compounds, such as dialkyl ether, 1,2-dimethoxyethane dioxane, tetrahydrofuran, N,N-dialkylated amides such as dimethylformamide, sulphoxides such as dimethylsulphoxide, nitriles such as acetonitrile, etc., and mixtures of such solvents with each other; for the ring closure reaction, it is also possible to use water or aqueous solvents.

The hydrazines of formula II can be used in the reaction also in the form of their addition salts with inorganic or organic acids, e.g. as addition salts with hydrochloric acid, sulphuric acid, acetic acid, oxalic acid, etc., It is necessary in this case to perform the addition reaction in a solvent or diluent, and with the addition of an acid-binding agent. Suitable as acid-binding agents are hydroxides and carbonates of alkali metals, as well as tertiary amines, e.g. trialkylamines, pyridine and pyridine bases, dialkylanilines, etc.

According to a variant of the process of the invention, an isothiocyanate of formula III is added to a hydrazone of the formula

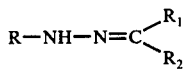   (V)

wherein

R has the meanings given under formula I,
$R_1$ represents hydrogen or alkyl, and
$R_2$ represents lower alkyl.

With the thiosemicarbazones, obtained as intermediates, of the formula

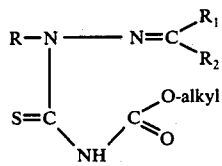   (VI)

there is subsequently performed, in an aqueous medium, preferably in the presence of acids, by which is meant mineral acids, organic acids and solutions of acid salts, the ring closure reaction to the 1,2,4-triazole of formula I. The use of a solvent or diluent, for example, one of the substances mentioned in the foregoing, or of mixtures of such substances with each other is necessary in the case of this variant.

The addition of the isothiocyanate to the hydrazine component is performed in a temperature range of $-40°$ to $+100°$ C., preferably at between 0° and 50° C. The ring closure is effected in a temperature range of 20° to 120° C.

The reactants are used in the process in equimolar amounts, whereby an excess of the one or of the other reactant can contribute towards obtaining the completion of the course of reaction.

The 1,2,4-triazole of formula I wherein R represents hydrogen has been hitherto obtained by a method given by F. Arndt F. Bielch (cp. Ber. Dtsch. Chem. Ges. 56, 2276-2283, (1923)). This method consists firstly of the reaction of thiosemicarbamide with methylthiocarbonyl chloride to the corresponding thiosemicarbazide-thiocarboxylic acid methyl ester, and the subsequent cyclisation of this in the presence of alkali to give 3-hydroxy-5-mercapto-1,2,4-triazole. The application of this method for obtaining 1,2,4-triazoles of formula I wherein R has a meaning other than hydrogen is rendered appreciably more difficult by virtue of the fact that the hydrazines substituted in the 1-position, which are required in this case, are not readily available. The difficulties arise in that in many cases, with use of the known methods for the preparation of thiosemicarbacides from substituted hydrazines, the thiocarbamoyl group is introduced not, as desired, in the 1-position but in the 2-position (cp. Acta Chemica Scandinavica 22 (1968), 1-50). Furthermore, in the preparation of 1,2,4-triazoles of formula I wherein R has a meaning other than hydrogen by the known method, one stage more than in the process according to the invention is required. It is therefore possible by the process according to the invention to obtain the 1,2,4-triazoles of formula I, valuable as intermediates for the preparation of pest control agents, in a more simple manner than hitherto and in better yields.

EXAMPLE 1

Preparation of ethoxycarbonylisothiocyanate 390 g of potassium isothiocyanate is placed into 3 liters of absolute acetone at 45° C. An addition is made to this dropwise at 45° to 50° C., in the course of half an hour, of 478 g of chloroformic acid ethyl ester. The reaction is slightly exothermic and a yellow suspension is formed. This is stirred for 2 hours at 50° C.; it is then cooled, filtered, washed, and and fully concentrated by evaporation in vacuo. The resulting residue after fractional distillation at 47° to 52° C./10 Torr is 425 g of crude yellow-orange ethoxycarbonylisothiocyanate.

EXAMPLE 2

Preparation of 1-methyl-3-hydroxy-5-mercapto-1,2,4-triazole

A mixture of 18.4 g of methylhydrazine and 400 ml of acetone is refluxed for 15 minutes. An addition is then made dropwise at 30° to 50° C. with stirring, of 52.4 g of ethoxycarbonylisothiocyanate (see Example 1), and the mixture refluxed for a further 15 minutes. The solvent is evaporated off to leave 80 g of a yellow oil; this is heated together with 60 ml of hydrochloric acid and 340 ml of water for 1½ hours at 90° C. The mixture is concentrated by evaporation to dryness, and the crystalline residue heated with 200 ml of acetonitrile. After cooling to 0° C., the whole is filtered to obtain 40.3 g of 1-methyl-3-hydroxy-5-mercapto-1,2,4-triazole in the form of white crystals, M.P. 264° to 268° C.

Analysis: Calculated: C, 27.5%; H, 3.8%; N, 32.0%; O, 12.2%; S, 24.5%. Found: C, 27.2%; H, 3.8%; N, 31.8%; O, 12.4%; S, 24.4%.

EXAMPLE 3

Preparation of 1-methyl-3-hydroxy-5-mercapto-1,2,4-triazole

An amount of 26.2 g of ethoxycarbonylisothiocyanate (see Example 1) is added to a solution of 9.2 g of methylhydrazine in 100 ml of acetonitrile, and the mixture refluxed for 18 hours; it is then cooled to 20° C. and the precipitated crystals filtered off. Recrystallisation yields 11 g of 1-methyl-3-hydroxy-5-mercapto-1,2,4-triazole having a melting point according to Example 2.

EXAMPLE 4

Preparation of 1-isopropyl-3-hydroxy-5-mercapto-1,2,4-triazole

An amount of 22.1 g of isopropylhydrazine hydrochloride is dissolved in a solution of 96 g of sodium hydroxide and 800 ml of water. After the addition of 300 ml of acetone, the mixture is refluxed for 30 minutes. While vigorous stirring is maintained, an addition is made dropwise at 20° to 30° C. of a solution of 262 g of ethoxycarbonylisothiocyanate (see Example 1) in 1000 ml of methylene chloride, and stirring then continued for 30 minutes at 40° C. The organic phase is separated and the solvent evaporated off in vacuo to obtain 394 g of a light-yellow oil, which is refluxed together with 500 ml of water and 10 ml of 2N hydrochloric acid for 2 hours. The whole is subsequently concentrated to dryness in vacuo, and the residue heated with 1000 ml of 10% acetic acid for 3 hours at 100° C. After cooling to 0° C., the precipitated crystals are filtered off: the yield is 132 g of 1-isopropyl-3-hydroxy-5-mercapto-1,2,4-triazole in the form of white crystals, M.P. 232° to 235° C.

Analysis: Calculated: C, 37.7%; H, 5.7%; S, 20.1%. Found: C, 37.4%; H, 5.8%; S, 19.8%.

EXAMPLE 5

Preparation of
1-ethyl-3-hydroxy-5-mercapto-1,2,4-triazole 30 g of ethylhydrazineoxalate and 30 ml of acetone are added to a solution of 9.6 g of sodium hydroxide in 150 ml of water. The mixture is refluxed for 10 minutes. While vigorous stirring is maintained, an addition is made dropwise at 20° to 30° C. of a solution of 26.2 g of ethoxycarbonylisothiocyanate (see Example 1) in 200 ml of methylene chloride, and the mixture then heated for 10 minutes at 40° C. The organic phase is separated, and the solvent evaporated off in vacuo to leave 37.5 g of a light-yellow oil; this is subsequently refluxed together with 50 ml of 2N hydrochloric acid and 150 ml of water for one hour. After cooling, the water is extensively evaporated off in vacuo, and the residue extracted with ethyl acetate. The ethyl acetate is evaporated off to leave a crystalline residue, which is washed with acetonitrile to obtain 10.3 g of 1-ethyl-3-hydroxy-5-mercapto-1,2,4-triazole as white crystals, M.P. 193° to 195° C.

Analysis: Calculated: C, 33.1%; H, 4.9%; N, 28.9%; S, 22.1%. Found: C, 33.4%; H, 5.0%; N, 26.6%; S, 22.1%.

EXAMPLE 6

Preparation of
1-isopropyl-3-hydroxy-5-mercapto-1,2,4-triazole

An amount of 27.5 g of ethoxycarbonylisothiocyanate (see Example 1) is added dropwise at 10° to 20° C., with stirring, to a solution of 22.8 g of isopropylacetonehydrazine in 100 ml of acetone, and stirring continued for 1 hour at room temperature. After removal of the solvent by evaporation, 48.9 g of 2-isopropyl-4-ethoxycarbonyl-acetone-thiosemicarbazone is obtained as a viscous yellow oil.

Analysis: Calculated: C, 48.9%; H, 7.8%; N, 17.1%; S, 13.0%. Found: C, 48.6%; H, 7.9%; N, 17.3%; S, 12.9%.

The product solidifies on standing and, after recrystallisation from cyclohexane, has the melting point 56° to 59° C. From this is obtained, by heating in aqueous hydrochloric acid, the triazole according to Example 4.

EXAMPLE 7

(a) Preparation of
2-phenyl-4-ethoxycarbonyl-acetone-thiosemicarbazone

An amount of 29.6 g of acetonephenylhydrazone (B.P. 74° to 75° C./0.01 Torr) is dissolved in 100 ml of absolute ether and 200 ml of petroleum ether (B.P. 50° to 70° C.). An addition in made dropwise at room temperature, in the course of half an hour, of 26.2 g of ethoxycarbonylisothiocyanate (see Example 1). The temperature increases by 3° C. and white crystals precipitate. The suspension is stirred for 15 hours at room temperature; the crystals are then filtered off, washed and dried. The yield is 33.8 g of 2-phenyl-4-ethoxycarbonyl-acetone-thiosemicarbazone, M.P. 117° to 117.5° C.

(b) Preparation of
1-phenyl-3-hydroxy-5-mercapto-1,2,4-triazole 27.9 g of pure 2-phenyl-4-ethoxycarbonyl-acetone-thiosemicarbazone is refluxed with 150 ml of water, 50 ml of ethanol and 3 ml of concentrated hydrochloric acid for 1 hour at 85° C. After cooling to 0° C., the precipitated crystals are filtered off, washed and dried. The resulting yield is 18.4 g of 1-phenyl-3-hydroxy-5-mercapto-1,2,4-triazole in the form of white crystals, M.P. 223° to 226° C.

EXAMPLE 8

Preparation of
1-phenyl-3-hydroxy-5-mercapto-1,2,4-triazole

An amount of 29.6 g of acetonephenylhydrazone is dissolved in 30 ml of dimethylsulphoxide. An addition is made dropwise within 20 minutes at 10° to 20° C. of 26.2 g of ethoxycarbonylisothiocyanate (see Example 1). The viscous yellow suspension is stirred for half an hour at room temperature; it is then diluted with 150 ml of ethanol and acidified with 3 ml of conc. hydrochloric acid (pH 1). The solution is refluxed for 1 hour; the ethanol is subsequently distilled off and the residue cooled to 0° C. After filtration, washing and drying, the yield is 28.3 g of pale yellow 1-phenyl-3-hydroxy-5-mercapto-1,2,4-triazole, M.P. 223° to 226° C.

The following compounds are prepared analogously to Examples 1 to 8:

$$\text{R-N-N} \atop \text{HS-}{\underset{N}{\parallel}}\text{-OH}$$

| R | Physical data |
|---|---|
| n-C$_3$H$_7$ | M.P.: 159–161° C |
| n-C$_4$H$_9$ | M.P.: 190–191° C |
| n-C$_{12}$H$_{25}$ | M.P.: 150–153° C |

EXAMPLE 9

Preparation of
O,O-diethyl-O-(1-methyl-5-propargylthio-1,2,4-triazolyl(3))-thiophosphoric acid ester from 1-methyl-5-propargylthio-3-hydroxy-1,2,4-triazole (a)
1-methyl-3-hydroxy-5-propargyl-mercapto-1,2,4-triazole 13.1 g of 1-methyl-3-hydroxy-5-mercapto-1,2,4-triazole and 13.1 g of propargylbromide are placed into 100 ml of ethanol. To this suspension is then added all at once an amount of 11.1 g of triethylamine. As a result of the exothermic reaction, the temperature rises to 45° C. A yellow product soon precipitates from the clear solution; the product is filtered off and washed with water. The undissolved material is dried over P$_2$O$_5$.

| Analysis: | Found: | Calculated: | M.P. 174 – 175° C |
|---|---|---|---|
| C | 42.6% | 42.59% | |
| H | 4.3% | 4.17% | |
| N | 24.6% | 24.83% | |

-continued

| Analysis: | Found: | Calculated: | M.P. 174 – 175° C |
|---|---|---|---|
| S | 19.5% | 18.95% | |

(b)
O,O-Diethyl-O-(1-methyl-5-propargylthio-1,2,4-triazolyl-(3)-thiophosphoric acid ester 16.9 g of 1-methyl-5-propargylthio-3-hydroxy-1,2,4-triazole and 13.8 g of potassium carbonate are refluxed in 300 ml of methyl ethyl ketone for 2 hours. The whole is then cooled to 40° C. and an addition made dropwise, within 10 minutes, of 19 g of diethylthiophosphoric acid chloride. The mixture is again refluxed for 2 hours and is subsequently cooled to room temperature; the insoluble salts are filtered off, and the filtrate concentrated in vacuo. The oil remaining behind is purified by chromatography through a silica gel column with chloroform as the eluant. The solvent is distilled off to obtain 27.3 g of light-yellow oil of the formula $$CH=C-CH_2-S-\underset{N}{\overset{CH_3-N-N}{\underset{\|}{\bigcirc}}}-O-\overset{S}{\underset{\|}{P}}(OC_2H_5)_2$$

This compound has an excellent action against insects such as, e.g. *Spodoptera littoralis; Leptinotarsa decemlineata; Aphis fabae; Chilo suppressalis; Aulacophora femoralis;* Pachmoda and Cortophila or representatives of the order acarina, such as, e.g. *Rhipicephalus bursa; Boophilus microplus* and *Tetranychus urticae;* as well as against *phytopathogenic nematodes,* such as, e.g. *Meloidogyne arenaria.*

What we claim is:

1. A process for the preparation of 1,2,4-triazoles of the formula $$HS-\underset{N}{\overset{R-N-N}{\underset{\|}{\bigcirc}}}-OH$$

wherein B represents hydrogen; straight-chain or branched $C_1-C_{18}$ alkyl optionally substituted by halogen, cyano, nitro, thiocyano, alkoxycarbonyl, N-alkylcarbamoyl, N,N-dialkyl carbamoyl, alkoxy or alkylthio; straight-chain or branched $C_3-C_8$ alkenyl or $C_3-C_8$ alkynyl, each optionally substituted by methyl or ethyl; phenyl optionally substituted by halogen, haloalkyl, nitro, alkyl, cyano, thiocyano, alkoxy, alkylthio, alkylsulphonyl, alkylsulphinyl, phenoxy, phenylthio, phenylsulphonyl, phenylsulphinyl, benzyloxy, benzylthio, benzylsulphonyl or benzylsulphinyl; naphthyl, benzyl, phenylethyl or phenylpropyl optionally, substituted by halogen, haloalkyl, nitro or alkyl; or $C_3-C_8$ cycloalkyl which can be bound by way of a methylene bridge member, or be substituted by an alkyl radical, lower alkyl being indicated for the alkyl groups in all of said substituted groups having an alkyl substituent; which process comprises adding, at a temperature of −40° to +100° C., a hydrazine of the formula

R—NH—NH$_2$ to an alkoxycarbonyl-isothiocyanate of the formula alkyl—O—CO—NCS and subsequently closing the triazole ring of the resulting thiosemicarbazide of the formula $$\underset{S=C-NH}{\overset{R-N-NH_2}{\phantom{xxx}}}C\underset{O}{\overset{O-alkyl}{\phantom{xx}}}$$

by splitting off an alkanol at a temperature of 20° to 120° C. in the presence of an inorganic or an organic acid or an acid salt.

2. Process according to claim 1, wherein the reactions are performed in the presence of a solvent or diluent.

3. Process according to claim 2, wherein the addition of isothiocyanate to the hydrazine component is performed in the presence of a ketone.

4. Process according to claim 1, wherein the hydrazine of the formula

R—NH—NH$_2$ is used in the form of an addition salt with inorganic or organic acids, and the addition reaction performed in the presence of an acid-binding agent.

5. A process for the preparation of 1,2,4-triazoles of the formula $$HS-\underset{N}{\overset{R-N-N}{\underset{\|}{\bigcirc}}}-OH$$

wherein R represents hydrogen; straight-chain or branched $C_1-C_{18}$ alkyl optionally substituted by halogen, cyano, nitro, thiocyano, alkoxycarbonyl, N-alkylcarbamoyl, N,N-dialkyl carbamoyl, alkoxy or alkylthio; straight-chain or branched $C_3-C_8$ alkenyl or $C_3-C_8$ alkynyl, each optionally substituted by methyl or ethyl; phenyl optionally substituted by halogen, nitro, alkyl, cyano, thiocyano, alkoxy, alkylthio, alkylsulphonyl, alkylsulphinyl, phenoxy, phenylthio, phenylsulphonyl, phenylsulphinyl, benzyloxy, benzylthio, benzylsulphonyl or benzylsulphinyl; naphthyl benzyl, phenylethyl or phenylpropyl optionally substituted by halogen, haloalkyl, nitro or alkyl; or $C_3-C_8$ cycloalkyl which can be bound by way of a methylene bridge member, or be substituted by an alkyl radical, lower alkyl being indicated for the alkyl groups in all of said substituted groups having an alkyl substituent; in which process a hydrazone of the formula $$R-NH-N=C\underset{R_2}{\overset{R_1}{\diagup}}$$

wherein
R has the above given meanings,
R$_1$ represents hydrogen or lower alkyl, and
R$_2$ represents lower alkyl,
is reacted in the presence of an inert solvent with an alkoxycarbonyl-isothiocyanate of the formula alkyl—O—CO—NCS to form a thiosemicarbazone of the formula

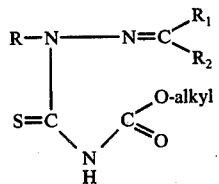
and this intermediate is subsequently heated in an aqueous medium in the presence of hydrochloric acid to effect ring closure.
* * * * *
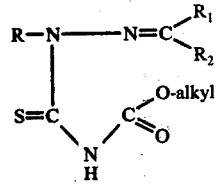
and this intermediate is subsequently heated in an aqueous medium in the presence of hydrochloric acid to effect ring closure.
* * * * *

UNITED STATES PATENT AND TRADEMARK OFFICE
CERTIFICATE OF CORRECTION

PATENT NO. : 4,123,437
DATED : October 31, 1978
INVENTOR(S) : Beat Böhner et al.

It is certified that error appears in the above-identified patent and that said Letters Patent are hereby corrected as shown below:

In Column 7, line 44, the letter B should be changed to R.

Column 10, lines 1 through 10 should be deleted.

Signed and Sealed this

Twentieth Day of March 1979

[SEAL]

Attest:

RUTH C. MASON
Attesting Officer

DONALD W. BANNER
Commissioner of Patents and Trademarks